United States Patent
Xie et al.

(10) Patent No.: US 9,464,972 B2
(45) Date of Patent: Oct. 11, 2016

(54) APPARATUS AND PROCEDURE FOR IN VITRO MEASUREMENT OF A SUBSTANCE, NICOTINE, RELEASED FROM A SMOKELESS TOBACCO PRODUCT

(76) Inventors: Jian-Ping Xie, Zhengzhou (CN); Ryan Q. Meng, Richland, WA (US); Jie Zhang, Zhengzhou (CN); Yong-Li Zong, Zhengzhou (CN); Peng Li, Zhengzhou (CN)

( * ) Notice: Subject to any disclaimer, the term of this patent is extended or adjusted under 35 U.S.C. 154(b) by 1288 days.

(21) Appl. No.: 13/041,217

(22) Filed: Mar. 4, 2011

(65) Prior Publication Data
US 2012/0222469 A1 Sep. 6, 2012

(51) Int. Cl.
| G01N 1/22 | (2006.01) |
| G01N 1/40 | (2006.01) |
| G01N 30/88 | (2006.01) |
| G01N 33/94 | (2006.01) |

(52) U.S. Cl.
CPC .............. *G01N 1/405* (2013.01); *G01N 30/88* (2013.01); *G01N 33/9406* (2013.01); *G01N 2030/884* (2013.01)

(58) Field of Classification Search
CPC ...... G01N 1/405; G01N 30/30; G01N 30/36; G01N 30/88; G01N 33/15; G01N 33/94; G01N 33/9406; G01N 33/944; G01N 2033/0091
USPC ........... 73/61.55–61.56, 61.59, 64.56, 865.6, 73/866; 422/70; 436/161, 178
See application file for complete search history.

(56) References Cited

U.S. PATENT DOCUMENTS

| 5,866,354 | A  | * | 2/1999 | Froman ........................ 435/29 |
| 2010/0047320 | A1 | * | 2/2010 | Prakash et al. ............... 424/439 |
| 2010/0233270 | A1 | * | 9/2010 | Mirkin et al. ................ 424/489 |
| 2010/0240086 | A1 | * | 9/2010 | Kashanin et al. .............. 435/29 |

FOREIGN PATENT DOCUMENTS

| CN | 101975833 A | * | 2/2011 | ............ G01N 30/36 |
| CN | 202330356 U | * | 7/2012 | ............ G01N 27/74 |

OTHER PUBLICATIONS

Jean-Yves Gal et al., About a synthetic saliva for in vitro studies, Talanta, 2001, 53, pp. 1103-115.*

(Continued)

*Primary Examiner* — Hezron E Williams
*Assistant Examiner* — Rodney T Frank
(74) *Attorney, Agent, or Firm* — Floyd E. Ivey

(57) ABSTRACT

An apparatus (100) and method for measuring an extract (1000) released from a product sample (330) in vitro. The apparatus (100) comprising an in vitro environment which simulates an in vivo environment. The apparatus (100) contains a product sample (330) with the product sample (330) exposed to the in vitro environment. An extract (1000) is produced from the product sample (330) when the product sample (330) is subjected to the in vitro environment. The extract (1000) is analyzed to determine the amount of at least one element in the extract and the rate of release of at least one element in the product sample (330). The product sample is a smokeless tobacco product. An element analyzed for is nicotine.

12 Claims, 5 Drawing Sheets

(56) References Cited

OTHER PUBLICATIONS

G. Alderbary et al., Determination of the in vitro disintegration profile of rapidly disintegrating tablets and correlation with oral disintegration, International Journal of Pharmaceutics, 2005 (available online Feb. 2005), 292, pp. 29-41.*

Jayachandar Gajendran et al., Product Performance Test for Medicated Chewing Gums, Dissolution Technologies, Aug. 2010, pp. 15-18, reprinted from 2004 publication.*

* cited by examiner

APPARATUS AND PROCEDURE FOR IN VITRO MEASUREMENT OF A SUBSTANCE, NICOTINE, RELEASED FROM A SMOKELESS TOBACCO PRODUCT

FIELD OF THE INVENTION

The present invention generally relates to an apparatus and method which extracts and measures the quantity of at least one substance from a sample. Further, the apparatus and method simulates the in vivo environment, to which a sample would be subjected, collects any fluid released from the sample and measures the quantity of at least one element within the fluid collected. This application includes the use of the apparatus and method in measuring the nicotine in a smokeless tobacco product. Yet more specifically, this invention relates to an apparatus and a method of extracting and measuring, in vitro, the release of nicotine from tobacco sachets utilizing artificial saliva thus mimicking or simulating the nicotine release from smokeless tobacco in the human mouth.

BACKGROUND OF THE INVENTION

Nicotine replacement therapy as an aid to quitting smoking has become increasingly popular. Smokeless tobacco products that are on the market include chewing tobacco, oral snuff, or tobacco sachets, which deliver nicotine to the buccal mucosa. Tobacco sachets, which are especially popular in Scandinavia and the United States, contain ground tobacco in packets that are sucked or held in the mouth.

The patents and publications referred to herein are provided herewith in an Information Disclosure Statement in accordance with 37 CFR 1.97.

SUMMARY OF THE INVENTION

The apparatus and method simulates an in vivo environment, to which a sample would be subjected, collects any fluid released from the sample and measures at least one element within the fluid collected.

BRIEF DESCRIPTION OF THE FIGURES

The foregoing and other features and advantages of the present invention will become more readily appreciated as the same become better understood by reference to the following detailed description of the preferred embodiment of the invention when taken in conjunction with the accompanying drawings, wherein.

DETAILED DESCRIPTION OF THE INVENTION

Figure 1:
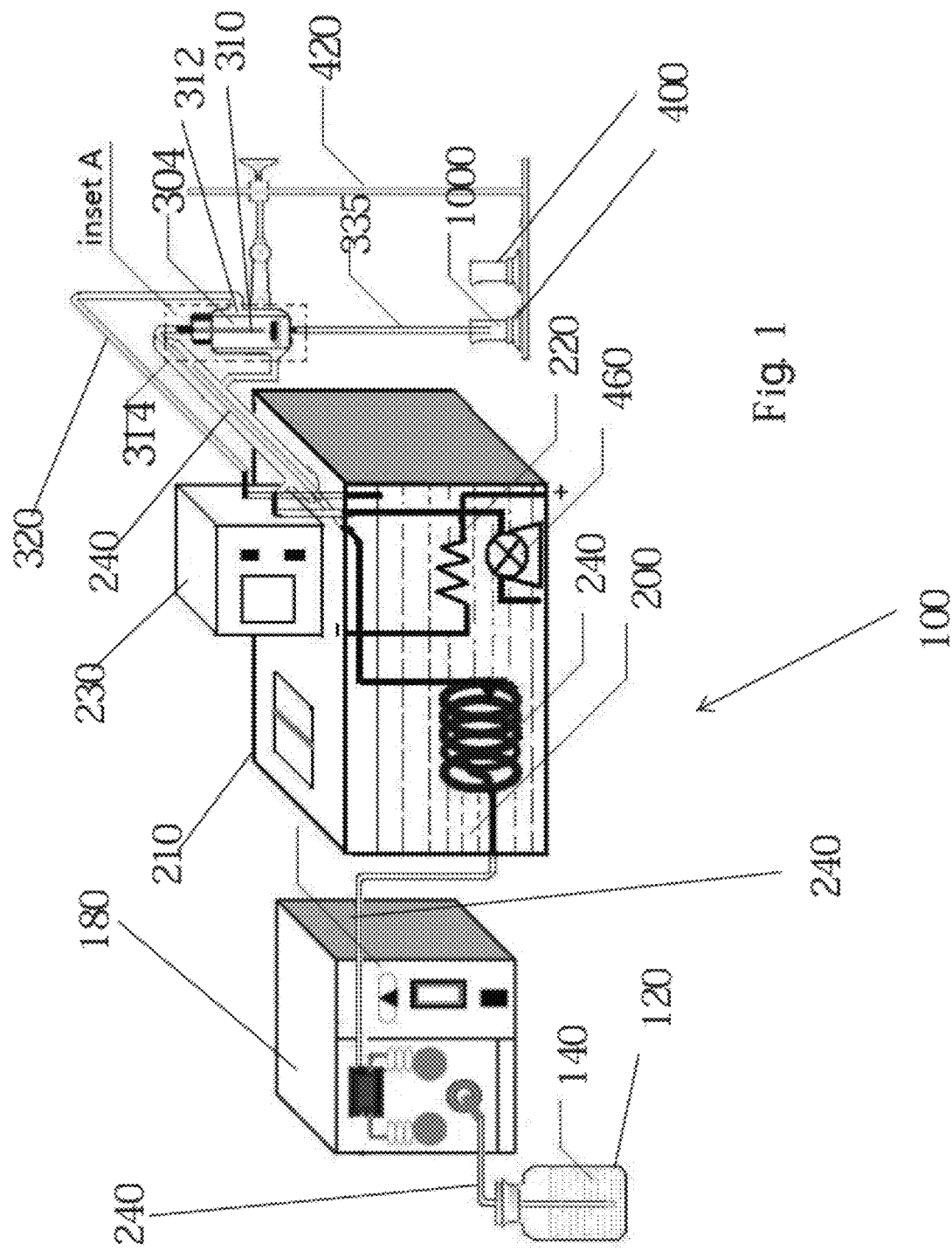
FIG. 1 illustrates the apparatus (100) showing the nicotine extraction and collection apparatus (100), a reservoir (120) for storage of a fluid (140), a fluid pump (180), tubing (240), a bath (200), a water bath tank (210), a recirculating pump (460), controls (230) for maintaining a heating or cooling element (220) at a temperature. Also illustrated is tubing (240) and tubing water jacket (314). Inset A is the extraction bottle 300. Also illustrated is a stand (420) supporting the extraction bottle (300). The bath (200) is a circulating temperature-regulating device and is usually a water bath (200).

FIG. 1 illustrates the apparatus (100) showing the nicotine extraction and collection apparatus (100), a reservoir (120) for storage of a fluid (140) which would be found in the vivo environment comprising, for nicotine measurement of sachets, artificial saliva. Also seen is a fluid pump (180) which transports the pumped fluid (140) through tubing (240) through a bath (200) which maintains the fluid (140) at a desired temperature. The fluid pump (180), in the preferred embodiment, allows regulation of the pump rate. Tubing (240), in the preferred embodiment, is composed of rigid, semi-rigid or flexible tubing. The bath (200), in the preferred embodiment is generally a circulating water bath contained in a water bath tank (210) having a heating and or cooling attribute to maintain the bath at a desired temperature, a recirculating pump and temperature control (230) for maintaining the heating or cooling element (220) at a temperature required to achieve the desired temperature of the bath (200). Where the environment is the human mouth the desired temperature to be maintained is 37° C. with this accomplished by means of the bath (200) having a heating or cooling element (220) within the bath (200) tank (210). The operation and use of a bath (200) as described herein and as illustrated will be known to those of ordinary skills in the water bath arts. Illustrated is tubing (240) which transports the fluid (140) pumped by fluid pump (180) from the reservoir (120) through the bath (200) and to an extraction bottle (300). The at least one extraction bottle (300) is described fully in the Brief Description for FIG. 2. An extraction bottle (300) has a water jacket (312) and tubing (240) has a tubing water jacket (314) encompassing the tubing (240) when the tubing (240) is outside of the bath (200) and is flowing to the extraction bottle water jacket (312). The bath (200) is circulated, by a recirculating pump (460), from the bath (200) contained within the bath tank (210) through the tubing water jacket (314), to the extraction bottle water jacket supply inlet (315), into the extraction bottle water jacket (312), out of the water jacket (312) via the water jacket return (320) and returned to the bath (200).

Figure 2:
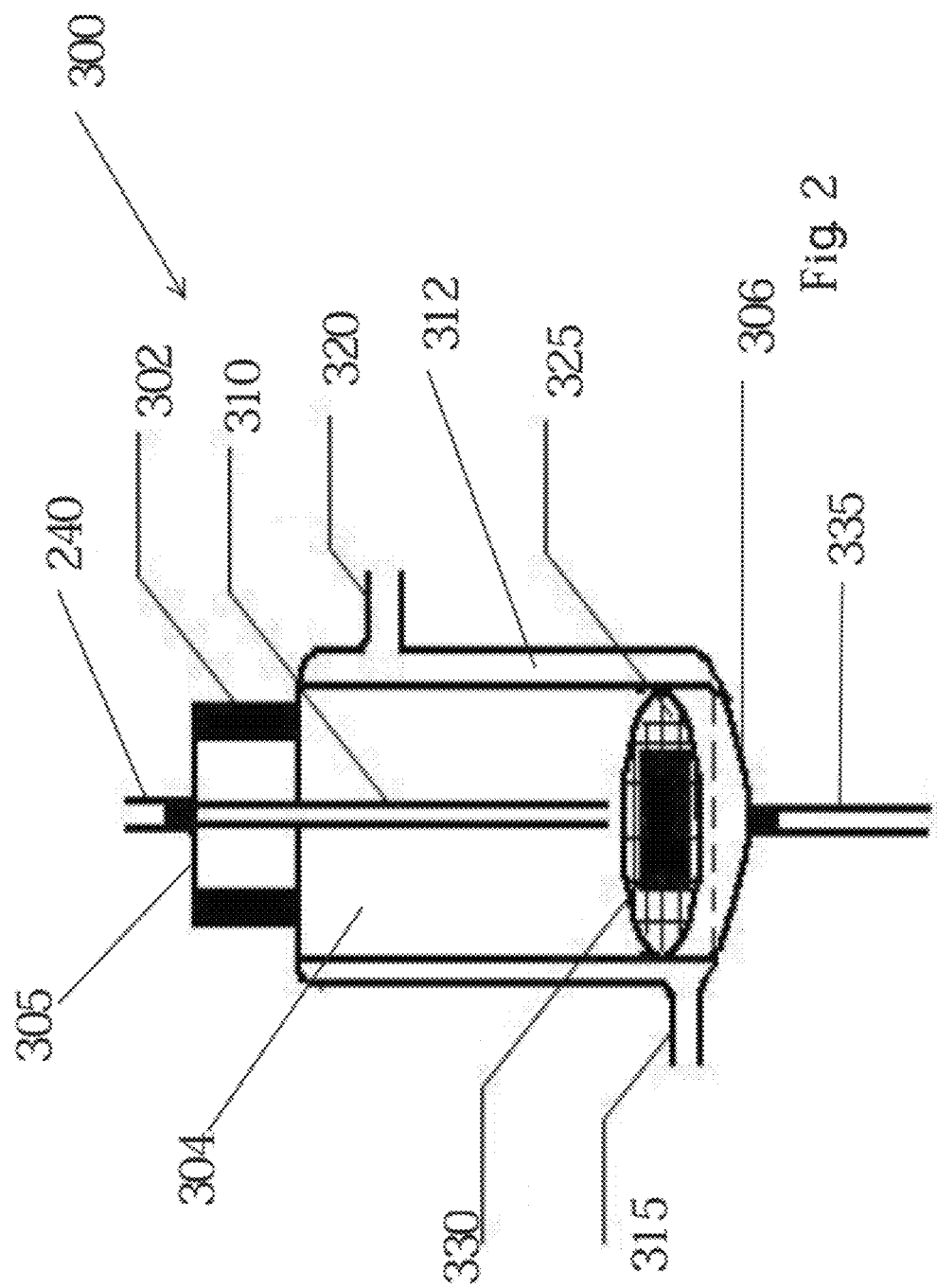
FIG. 2 illustrates the extraction bottle (300) showing tubing (240), an extraction bottle top (302), an extraction bottle interior (304), an extraction bottle cap (305), an extraction bottle bottom (306), a supply tube (310), an extraction bottle water jacket (312), an extraction bottle water jacket supply inlet (315), an extraction bottle water jacket return (320), a screen mesh (325), a product sample (330) and a collection tube, (335).

FIG. 2 illustrating the extraction bottle (300) having an extraction bottle top (302), an extraction bottle bottom (306) and an extraction bottle interior (304). An extraction bottle cap (305) is shaped to be friction fitted at the extraction bottle top (302), the extraction bottle cap (305) having an aperture at which or into which tubing (240) is friction fitted or affixed by tubing fixing means including clamps, connectors and other methods readily known to those of ordinary skills in apparatus and chemical arts. A supply tube (310) downwardly extends, from the extraction bottle cap (305), into the extraction bottle interior (304). The fluid (140) transported via tubing (240) flows into and through the supply tube (310). Downwardly and distal to the extraction bottle top (302) and the supply tube (310) is a collection tube (335) which is downwardly extending from an extraction bottle bottom (306). A screen mesh (325) is affixed by affixing means within the extraction bottle interior (304) intermediate the supply tube (310) and the extraction bottle bottom (306). A product sample (330) is placed on or affixed to the screen mesh (325) in alignment with the supply tube (310) so that the fluid (140) from the supply tube (310) is flowed or dripped onto the product sample (330). The extract (1000) from the combination of the fluid (140) and the sample (330) is drained from the extraction bottle (300) by a collection tube (335) and is then deposited into at least one collection bottle (400). An extraction bottle water jacket (312) substantially encloses the extraction bottle (300). The extraction bottle water jacket (312) has an extraction bottle water jacket supply inlet (315) and an extraction bottle water jacket return (320).

Description of the Procedure

The nicotine extraction and collection procedure include the following steps:

1. Add fluid (140) to the reservoir (120). Fluid (140) is artificial saliva where the extraction is nicotine from a smokeless tobacco product;

2. Set the bath (200) and the heating or cooling element (220) temperature control (230) to the temperature desired as established from the in vivo environment. Where the fluid (140) is artificial saliva and, for the measurement of nicotine in a smokeless tobacco product, set the temperature to 37° C.;

3. Start the fluid pump (180) and set the pump to the desired pump rate. For measurement of nicotine in the preferred embodiment of this invention set the pump (180) to pump at 0.1 to 7 ml/min based on experiment requirement;

4. When the temperature and flow rate are stabilized, add the product sample (330) to extraction bottle interior (304) onto the screen mesh (325). Where the product sample is for a smokeless tobacco product sample (330) the product sample (330) is a smokeless tobacco sachet; the product sample (330) is placed onto the screen mesh (325) in alignment with the supply tube (310);

5. The fluid (140) from the supply tube (310) is flowed or dripped onto the product sample (330) producing an extract (1000) from the combination of the fluid (140) and the sample (330) which is drained from the extraction bottle (300) by a collection tube (335) and is then deposited into at least one collection bottle (400) at intervals determined by experimental design. Where the product sample (330) is a smokeless tobacco product sample (330) 1-n collection bottles (400) will used with bottles (400) changed at intervals of 1-5 min based on experimental design;

6. Extract the residual element from the product sample (330) by placing the product sample (330) in solvent effective for the type of product sample (330); where the product sample (330) is a smokeless tobacco product, the solvent in the preferred embodiment is 20 to 50 ml ethanol:5% NaOH mixture (9:1), and extract with ultrasound for 30 min.

7. Measure the target element in the extract (1000) by use of a measuring instrument suitable for the attributes of the target element in the extract (1000); for the preferred embodiment when the target element is nicotine from a smokeless tobacco product the measuring instrument is high-performance liquid chromatography (HPLC); the extract (1000) of nicotine in artificial saliva and the residual nicotine from ethanol NaOH mixture are determined using HPLC in the following conditions:

1. Chromatograph column is a C18 reverse phase column
2. Mobile phase is methanol and 20 mmol phosphate buffer (23:77, volume to volume) with 0.2% Triethylamine, pH=6.0
3. Flow rate is 1 ml/min
4. Column temperature is 35° C.

Examples of Application

Example 1

Artificial saliva temperature was maintained at 37° C., pump flow rate 1 ml/min. Artificial saliva was made using the formula in Table 1, with a pH of 6.7. The artificial saliva collection intervals were at 1, 2, 3, 4, 5, 6, 7, 8, 9, 10, 12, 14, 16, 18, 20, 24, 28, 32 minutes after the extraction started.

TABLE 1

Recipe for Artificial Saliva

| Components | Concentrations (g/L) | Components | Concentrations (g/L) |
|---|---|---|---|
| NaCl | 1.550 | KHCO$_3$ | 2.352 |
| KCl | 0.865 | MgCl$_2$ | 0.715 |
| Na$_2$HPO$_4$ | 1.717 | CaCl$_2$ | 0.358 |
| KH$_2$PO4 | 0.765 | NaHCO$_3$ | 630.8 |
| Citric acid | 0.120 | | |

The recipe is from Jayachandar et al. (Dissolution Technologies, 2004, 11 (2): 12-15).

Figure 3:
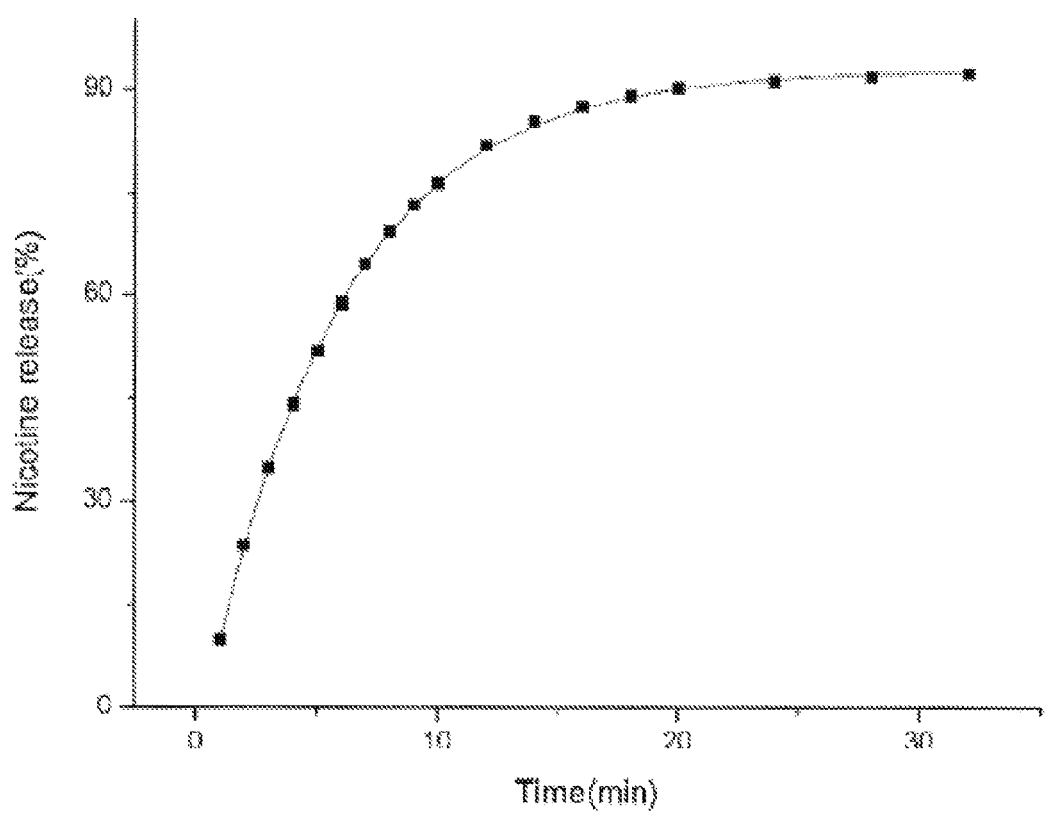
FIG. 3 shows the graphical illustration of the measurement of nicotine from a smokeless tobacco product addressed in Table 1 with the use of artificial saliva recipe from Jayachandar, Gajendran, 1, Kraemer, J., and Knudsen, S. R. 2004. Product Performance Test for Medicated Chewing Gums. Dissolution Technologies, 2004, 11 (2):12-15).

A nicotine release with extraction time curve was generated (FIG. 3). Total nicotine is the sum of all collection bottles plus the residual nicotine in the tobacco. Under this extraction condition, nicotine release was rapid in the first 5 minutes, and gradually slowed down. In the first 5 minutes, the average rate of nicotine release was approximately 10%; from 6 min to 10 min, the average rate of nicotine release was approximately 4.3%; from 11 min to 20 min, the average rate of nicotine release was approximately 1%. After 20 min of extraction, over 90% of nicotine was released from tobacco, and very little nicotine was collected from the 20 to 32 min extraction period.

FIG. 3. shows the extraction time and nicotine release where the X-axis is the time interval of nicotine elution solution collection and the Y-axis is the percent of accumulated nicotine release over time.

Example 2

Artificial saliva temperature was maintained at 37° C., pump flow rate 2 ml/min. Artificial saliva was made using the formula in Table 2, with a pH of 7.0. The artificial saliva collection intervals were at 1, 2, 3, 4, 5, 6, 7, 8, 9, 10, 12, 14, 16, 18, 20, 22, 24, 26, 28, 30 minutes after the extraction start.

TABLE 2

Recipe of Artificial Saliva

| Components | Concentrations mg/L | Components | Concentrations mg/L |
|---|---|---|---|
| NaCl | 125.6 | $Na_2SO_4 \cdot 10H_2O$ | 763.2 |
| KCl | 963.9 | $NH_4Cl$ | 178 |
| KSCN | 189.2 | $CaCl_2$ | 227.8 |
| $KH_2PO_4$ | 654.5 | $NaHCO_3$ | 630.8 |
| Urea | 200 | | |

The recipe is from Gal et al., (Talanta, 2001, 53: 1103-1115)

Figure 4:
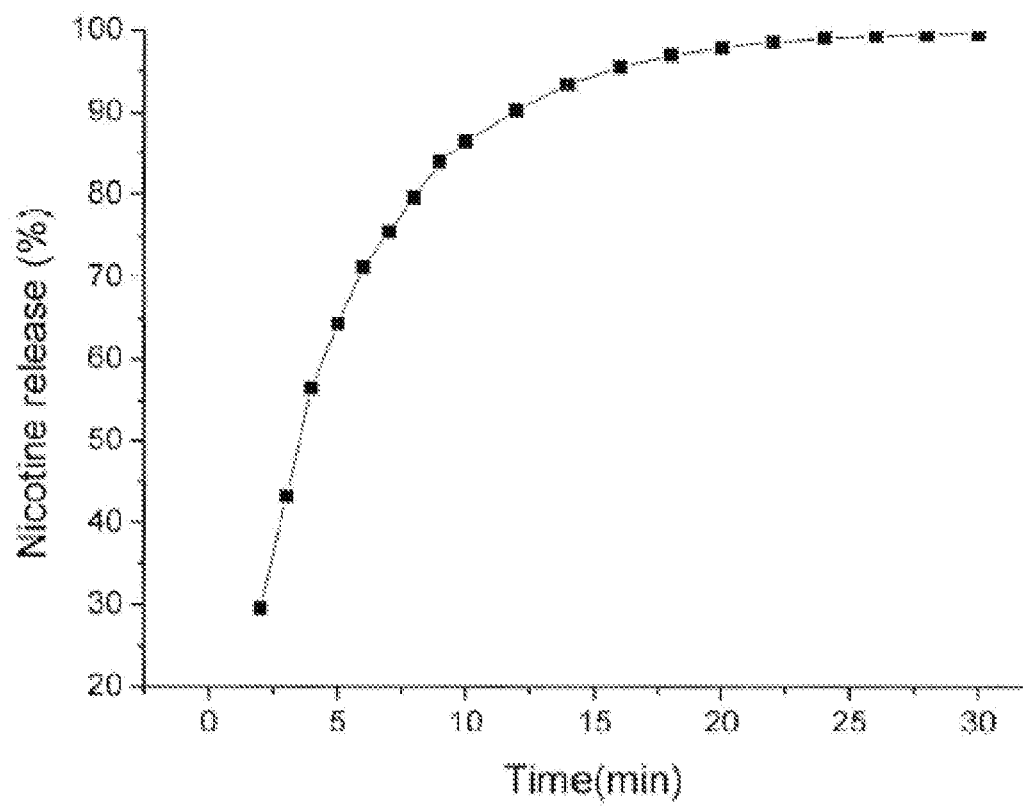
FIG. 4 shows the graphical illustration of the measurement of nicotine from a smokeless tobacco product addressed in Table 2 with the use of artificial saliva recipe from Gal, I. Y., Fovet, Y., Adib-Yadzi, M. 2001. About a synthetic saliva for in vitro studies. Talanta, 53:1103-1115.

A nicotine release with extraction time curve was generated (FIG. 4). Total nicotine is the sum of all collection bottles plus the residual nicotine in the tobacco. Under this extraction condition, nicotine release was rapid in the first 5 minutes, and gradually slowed down. In the first 5 minutes, 64% nicotine was release; from 6 min to 10 min, another 20% nicotine was released; In the first 20 min of extraction, over 95% of nicotine was released from tobacco, and very little nicotine was collected from the 20 to 30 min extraction period. The overall nicotine extraction efficiency was slightly better in example 2 compared to example 1.

FIG. 4. shows extraction time and nicotine release where the X-axis is the time interval of nicotine elution solution collection and the Y-axis is the percent of accumulated nicotine release over time and where the recipe is from Gal et al., (Talanta, 2001, 53:1103-1115).

Example 3

Artificial saliva temperature was maintained at 37° C., pump flow rate 4 ml/min. Artificial saliva was made using the formula in Table 3, with a pH of 5.8. The artificial saliva collection intervals were at 2, 4, 6, 7, 8, 10, 12, 14, 16, 18, 20, 24, 28, and 32 minutes after the extraction start.

TABLE 3

Recipe of Artificial Saliva

| Components | Concentrations (g/L) | Components | Concentrations (g/L) |
|---|---|---|---|
| NaCl | 0.4 | $Na_2SO_4 \cdot 10H_2O$ | 763.2 |
| KCl | 0.4 | $CaCl_2 \cdot 2H_2O$ | 0.8 |
| $NaS \cdot 9H_2O$ | 0.005 | $NaH_2PO_4$ | 0.78 |
| Urea | 1 | | |

The recipe is from Abdelbary, G., et. al. International journal of pharmaceutics, 292(1-2): 29-41.

Figure 5:
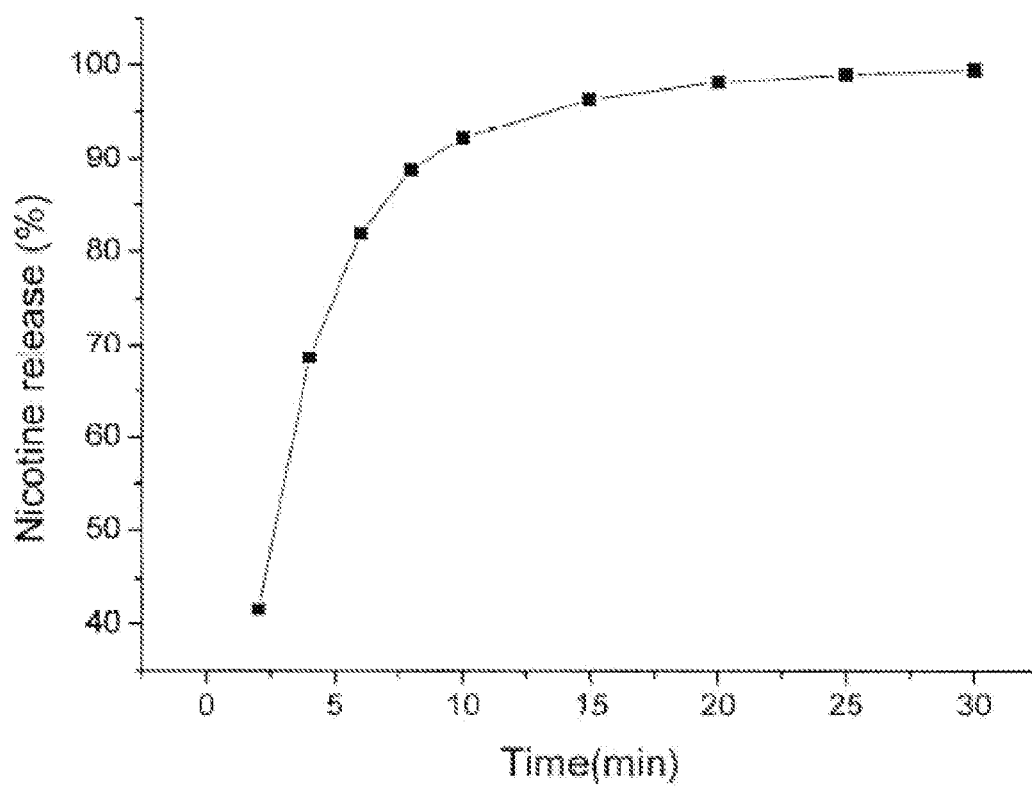
FIG. 5 shows the graphical illustration of the measurement of nicotine from a smokeless tobacco product addressed in Table 3 with the use of artificial saliva recipe from Abdelbary, G., Eouani, C., Prinderre, P., Joachim, J., Reynier J. P., Piccerelle, P. H. 2005. Determination of the in vitro disintegration profile of rapidly disintegrating tablets and correlation with oral disintegration. International Journal of Pharmaceutics, 292 (1-2):29-41.

A nicotine release with extraction time curve was generated (FIG. 5). Total nicotine is the sum of all collection bottles plus the residual nicotine in the tobacco. Under this extraction condition, nicotine release was 82% in the first 6 min; 92% in the first 10 min. The rate of nicotine release was faster than in examples 1 and 2.

FIG. 5 shows extraction time and nicotine release where X-axis is the time interval of nicotine elution solution collection and the Y-axis is the percent of accumulated nicotine release over time.

While various embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims. Various features of the invention are set forth in the appended claims.

I claim:

1. An apparatus (100) for measuring an extract (1000) released from a product sample (330) in vitro comprising:
an apparatus (100) comprising an in vitro environment which simulates an in vivo environment; and
the apparatus (100) containing a product sample (330) with the product sample (330) exposed to the in vitro environment; and
an extract (1000) is produced from the product sample (330) when the product sample (330) is subjected to the in vitro environment; and the extract (1000) is analyzed to determine the amount of at least one element in the extract; and the apparatus (100) comprises an extraction and collection apparatus (100); a reservoir (120) contains a fluid (140) which simulates a fluid found in an in vivo environment; a fluid pump (180) transports the fluid (140) through tubing (240) through a bath (200) where the bath (200) maintains the fluid (140) within a desired temperature range; the desired temperature is maintained by a heating or cooling element (220) within the bath (200); the fluid is (140) is transported via tubing (240) by the fluid pump (180) from the bath (200) into an extraction bottle (300) where the fluid (140) is deposited onto a product sample (330); an extract (1000) from the combination of the fluid (140) and the sample (330) is drained from the extraction bottle (300) and is deposited into at least one collection bottle (400); the extract (1000) is analyzed for measurement of at least one element.

2. The apparatus (100) for measuring an extracted substance of claim 1 further comprising:
the extraction bottle (300) has an extraction bottle top (302), an extraction bottle interior (304); an extraction bottle cap (305) and an extraction bottle bottom (306);
the fluid (140) is transported to the extraction bottle top (302) and through a supply tube (310) downwardly extending from the extraction bottle top (302);
a screen mesh (325) is fitted within the extraction bottle interior (304) intermediate the supply tube (310) and the extraction bottle bottom (306);
a product sample (330) is placed on the screen mesh (325) in alignment with the supply tube (310);
a collection tube (335) is downwardly extending from the extraction bottle bottom (306) with the extract (1000) deposited from the collection tube (335) into at least one collection bottle (400).

3. The apparatus for measuring an extracted substance of claim 1 further comprising:
wherein the bath (200) is a circulating temperature-regulating device, wherein the fluid (140) is pumped via tubing (240) by the pump (180) through the water-bath (200) and to and into the extraction bottle (300); the water-bath (200) contains a heating or cooling element (220) that heats the bath (200) and the fluid (140) flowing via tubing (240) to 37° C.; the fluid (140) is artificial saliva (140).

4. The apparatus for measuring an extracted substance of claim 3, wherein said pump (180) pumps said artificial saliva (140) from said reservoir (120) through the bath (200), thereby heating or cooling said artificial saliva (140) to 37° C.

5. The apparatus for measuring an extracted substance of claim 1, wherein the product sample (330) is a smokeless tobacco product (330) and is a tobacco sachet (330); and
the fluid (140) is artificial saliva; and
(140) the bath (200) contains a recirculating pump (460) which re-circulates the bath (200) through tubing water jacket (314) and extraction bottle water jacket (312) and returns to the bath (200); and the at least one collection bottle (400) comprises 1-n collection bottles (400) where "n" is determined by the number of samples taken; and the extract (1000) is analyzed for quantity of nicotine in the product sample (330) and the rate of release of nicotine in the product sample; and the analysis of the nicotine is by use of High-performance liquid chromatography (HPLC).

6. A method for measuring an extract (1000) released from a product sample (330) in vitro comprising:

creating an in vitro environment which simulates an in vivo environment; and subjecting a product sample (330) to the in vitro environment; and collecting an extract (1000) resulting from the product sample (330) being subjected to the in vitro environment; and analyzing the extract (1000) to determine the amount of at least one element in the extract (1000); and the in vitro environment is a fluid (140); adding the fluid (140) to a reservoir (120); and setting a bath (200) to a desired temperature; and pumping the fluid (140), via tubing (240), through said bath (200);

and stabilizing the temperature and flow rate of the fluid (140); adding a product sample (330) to an extraction bottle (300); and pumping the fluid (140) to said extraction bottle (300) and dripping the fluid (140) onto the product sample (330); and collecting an extract (1000) from the product sample (330) in individual bottles (400) in time intervals based on experimental design; and extracting, following the concluding time interval, the residual extract (1000) from the product sample (330) by placing the product sample (330) in a solvent and measuring the extract (1000) for the quantity of at least one element extracted during each time interval and measuring the residual extract (1000) from the product sample;

measuring the quantity of at least one element from the product sample (330) in each bottle with a measuring instrument and measuring the residual and the residual quantity of at least one element from the product sample with a measuring instrument.

7. The method of claim 6 measuring at least one element using the collection apparatus (100) of this invention further comprising:

first, the in vitro environment is an artificial *salvia* (140); adding the artificial saliva (140) to a reservoir (120); and second, setting a bath (200) to a temperature of 35° to 37° C.; and third, pumping the artificial *salvia* (140) with a pump (180), via tubing (240) through said bath (200); and fourth, stabilizing the temperature to a temperature of 35° to 37° C. and the flow rate of the artificial *salvia* (140) to a rate of 0.1 to 7 ml/min; and adding a smokeless tobacco product sample (330) to an extraction bottle (300); and fifth, pumping the artificial *salvia* (140) to said extraction bottle (300) and dripping the artificial *salvia* (140) onto the smokeless tobacco product sample (330); and sixth, collecting an extract (1000) from the smokeless tobacco product sample (330) in individual bottles (400) at time intervals of 1 to 5 minutes; and seventh, extracting, following the concluding time interval, the residual extract (1000) from the smokeless tobacco product sample (330) by placing the smokeless tobacco product sample (330) in a solvent and measuring the extract (1000) for the quantity of at least one element extracted during each time interval and measuring the residual extract (1000) from the product sample;

eighth, measuring the quantity of nicotine from the smokeless tobacco product sample (330) in each bottle with a measuring instrument and measuring the residual and the residual quantity of at least one element from the product sample with a measuring instrument.

8. The method of claim 7 measuring at least one element using the collection apparatus (100) apparatus of this invention further comprising:

the at least one element is nicotine where the product sample is a smokeless tobacco product sample (330); and the measuring instrument technique is chromatographic comprising High-performance liquid chromatography (HPLC); and the solvent is 20 to 50 ml ethanol, 5% NaOH mixture (9:1), and extract with ultrasound for 30 min.

9. An apparatus (100) for measuring an extract (1000) released from a product sample (330) in vitro comprising:

an apparatus (100) comprising an in vitro environment which simulates an in vivo environment; and the apparatus (100) containing a product sample (330) with the product sample (330) exposed to the in vitro environment; and an extract (1000) is produced from the product sample (330) when the product sample (330) is subjected to the in vitro environment; and the extract (1000) is analyzed to determine the amount of at least one element in the extract; and the apparatus (100) comprises an extraction and collection apparatus (100); a reservoir (120) contains a fluid (140) which simulates a fluid found in an in vivo environment;

a fluid pump (180) transports the fluid (140) through tubing (240) through a bath (200) where the bath (200) maintains the fluid (140) within a desired temperature range; a desired temperature is maintained by a heating or cooling element (220) within the bath (200);

the fluid is (140) is transported via tubing (240) by the fluid pump (180) from the bath (200) into an extraction bottle (300) where the fluid (140) is deposited onto a product sample (330);

an extract (1000) from the combination of the fluid (140) and the sample (330) is drained from the extraction bottle (300) and is deposited into at least one collection bottle (400);

the extract (1000) is analyzed for measurement of at least one element; and the extraction bottle (300) has an extraction bottle top (302), an extraction bottle interior (304); an extraction bottle cap (305) and an extraction bottle bottom (306); the fluid (140) is transported to the extraction bottle top (302) and through a supply tube (310) downwardly extending from the extraction bottle top (302); a screen mesh (325) is fitted within the extraction bottle interior (304) intermediate the supply tube (310) and the extraction bottle bottom (306);

a product sample (330) is placed on the screen mesh (325) in alignment with the supply tube (310);

a collection tube (335) is downwardly extending from the extraction bottle bottom (306) with the extract (1000) deposited from the collection tube (335) into at least one collection bottle (400).

10. An apparatus (100) for measuring an extract (1000) released from a product sample (330) in vitro comprising:

an apparatus (100) comprising an in vitro environment which simulates an in vivo environment; and the apparatus (100) containing a product sample (330) with the product sample (330) exposed to the in vitro environment; and an extract (1000) is produced from the product sample (330) when the product sample (330) is subjected to the in vitro environment; and the extract (1000) is analyzed to determine the amount of at least one element in the extract; and a. circulating temperature-regulating device is a water-bath (200); and the fluid (140) is pumped via tubing (240) by the pump (180) through the water-bath (200) and to and into an extraction bottle (300); the water-bath (200) contains a heating or cooling element (220) that heats the bath (200) and the fluid (140) flowing via tubing (240) to 37° C.; the fluid (140) is artificial saliva (140); and said pump (180) pumps said artificial saliva (140) from said reservoir (120) through the bath (200), thereby heating or cooling said artificial saliva (140) to 37° C.; and the bath (200) contains a recirculating pump (460) which re-circulates the bath (200) through tubing water jacket (314) and extraction bottle water jacket (312) and returns to the bath (200); and the at least one collection bottle (400) comprises 1-n collection bottles (400) where "n" is determined by the number of samples taken; and the extract (1000) is analyzed for quantity of nicotine in the product sample (330) and the rate of release of nicotine in the product sample; and the analysis of the nicotine is by use of High-performance liquid chromatography (HPLC).

11. A method for measuring an extract (1000) released from a product sample (330) in vitro comprising:

creating an in vitro environment which simulates an in vivo environment; and subjecting a product sample (330) to the in vitro environment; and collecting an extract (1000) resulting from the product sample (330) being subjected to the in vitro environment; and analyzing the extract (1000) to determine the amount of at least one element in the extract (1000); and the in vitro environment is a fluid (140); adding the fluid (140) to a reservoir (120); and setting a bath (200) to a desired temperature; and pumping the fluid (140), via tubing (240), through said bath (200); and stabilizing the temperature and flow rate of the fluid (140); adding a product sample (330) to an extraction bottle (300); and pumping the fluid (140) to said extraction bottle (300) and dripping the fluid (140) onto the product sample (330); and collecting an extract (1000) from the product sample (330) in individual bottles (400) in time intervals based on experimental design; and extracting, following a concluding time interval, any remaining extract (1000) from the product sample (330) by placing the product sample (330) in a solvent and measuring the extract (1000) for the quantity of at least one element extracted during each time interval and measuring the residual extract (1000) from the product sample; and measuring the quantity of at least one element from the product sample (330) in each bottle with a measuring instrument and measuring the residual and the residual quantity of at least one element from the product sample with a measuring instrument.

12. A method for measuring an extract (1000) released from a product sample (330) in vitro comprising:

creating an in vitro environment which simulates an in vivo environment; and subjecting a product sample (330) to the in vitro environment; and collecting an extract (1000) resulting from the product sample (330) being subjected to the in vitro environment; and analyzing the extract (1000) to determine the amount of at least one element in the extract (1000);

the in vitro environment is an artificial *salvia* (140); adding the artificial saliva (140) to a reservoir (120); and setting a bath (200) to a temperature of 35° to 37° C.; and pumping the artificial *salvia* (140) with a pump (180), via tubing (240) through said bath (200); and stabilizing the temperature to a temperature of 35° to 37° C. and the flow rate of the artificial *salvia* (140) to a rate of 0.1 to 7 ml/min; and adding a smokeless tobacco product sample (330) to an extraction bottle (300); and pumping the artificial *salvia* (140) to said extraction bottle (300) and dripping the artificial *salvia* (140) onto the smokeless tobacco product sample (330); and collecting an extract (1000) from the smokeless tobacco product sample (330) in individual bottles (400) at time intervals of 1 to 5 minutes; and extracting, following a concluding time interval, any remaining extract (1000) from the product sample (330) from the smokeless tobacco product sample (330) by placing the smokeless tobacco product sample (330) in a solvent and measuring the extract (1000) for the quantity of at least one element extracted during each time interval and measuring the residual extract (1000) from the product sample;

measuring the quantity of nicotine from the smokeless tobacco product sample (330) in each bottle with a measuring instrument and measuring the residual and the residual quantity of at least one element from the product sample with a measuring instrument; and the at least one element is nicotine where the product sample is a smokeless tobacco product sample (330); and the measuring instrument technique is chromatographic comprising High-performance liquid chromatography (HPLC); and the solvent is 20 to 50 ml ethanol, 5% NaOH mixture (9:1), and extract with ultrasound for 30 min.

* * * * *